US006362225B1

(12) United States Patent
Andreakos

(10) Patent No.: US 6,362,225 B1
(45) Date of Patent: Mar. 26, 2002

(54) TARGET THERAPIES FOR TREATING COMMON VIRAL INFECTIONS

(76) Inventor: George Andreakos, HC 1 Box 207, Honesdale, PA (US) 18431

( * ) Notice: Subject to any disclaimer, the term of this patent is extended or adjusted under 35 U.S.C. 154(b) by 0 days.

(21) Appl. No.: 09/478,722

(22) Filed: Jan. 6, 2000

Related U.S. Application Data

(63) Continuation-in-part of application No. 09/234,825, filed on Jan. 21, 1999, now abandoned.
(51) Int. Cl.⁷ .................. A61K 31/195; A61K 9/00; A61K 7/00; A61K 9/20
(52) U.S. Cl. .................. 514/561; 424/43; 424/46; 424/464; 514/958; 514/959
(58) Field of Search ................ 424/464, 43, 46; 514/561, 958, 959

(56) References Cited

U.S. PATENT DOCUMENTS

| | | | | |
|---|---|---|---|---|
| 4,405,610 | A | | 9/1983 | Krnjević .................. 424/180 |
| 4,415,590 | A | * | 11/1983 | Gerzon .................. 424/319 |
| 4,476,116 | A | | 10/1984 | Anik .................. 424/177 |
| 4,937,234 | A | | 6/1990 | Fahim .................. 514/53 |
| 5,508,282 | A | | 4/1996 | Tulin-Silver et al. ....... 514/264 |
| 5,641,889 | A | * | 6/1997 | Daluge .................. 564/1 |
| 6,136,294 | A | * | 10/2000 | Adjei .................. 425/45 |

OTHER PUBLICATIONS

Murray et al. "textbook of Respiratory Medicine," 1994, W.B. Saunders Company, pp. 995–998.*
CAplus Abstract, AN 94102090, Cappella et al. 1994.*
Fields et al. Virology, 1995, Lippincott Williams & Wilkins, Third Edition, pp. 722–723.*
Herpes Virus: The Great Masquerader, Christina Ferroli Saturday Evening Post Nov.–Dec. 1995 v267 n6 p56.
A Microbidogist who Stopped Her Fever Blisters, Ted Krieter Saturday Evening Post Nov.–Dec. 1995 v267 n6 p54.
The Metabolic Roles, Pharmacology, and Toxicology of Lysine N.W. Flodin; J. Am. Coll. Nutr. Feb. 1997 p 7.

* cited by examiner

*Primary Examiner*—Russell Travers
*Assistant Examiner*—Shengjun Wang
(74) *Attorney, Agent, or Firm*—Sandra M. Kotin

(57) ABSTRACT

Therapies and compositions are described for use in the treatment of a variety of common viral infections such as those of the upper respiratory tract, eye, stomach and intestines, and such viral lesions as cold sores, canker sores and those caused by genital herpes. The effective ingredient in the various therapies and compositions is the compound L-Lysine monohydrochloride (lysine). The crystalline lysine is ground into a fine powder and dispersed in a variety of aqueous media and other carrier systems. A solution in the form of a spray is administered to the nasal membranes, the mouth and throat, and to the lungs. Lozenges are designed to be dissolved in the mouth, both above the tongue and sublingually, and gels and solutions are applied directly to the lesions. Lysine is also administered in the form of drops, chewing gum, suppositories and by enema. In microcrystalline powder form the lysine may be administered directly into the lungs. When used at specified time intervals throughout each 24 hour period the duration of the symptoms of the viral infections is noticeably diminished. There are no side effects and no toxic levels of lysine. The various compositions are quite stable.

43 Claims, No Drawings

TARGET THERAPIES FOR TREATING COMMON VIRAL INFECTIONS

This application is a continuation-in-part of my United States application for Letters Patent Ser. No. 09/234,825 entitled "Composition and Method for Treating Common Viral Infections" filed on Jan. 21, 1999 now abandoned.

FIELD OF THE INVENTION

The instant invention relates to therapies and compositions for treating a variety of viral infections, most specifically viral infections that affect mucous membranes.

BACKGROUND OF THE INVENTION

Most people, at one time or another, are at risk for a variety of viral infections, some resulting in running nose, cough, sinus inflamation, sore throat, and ear fullness. These symptoms are often a part of what is usually called "the common cold" and are also associated with many forms of influenza. A variety of digestive problems or stomach upsets may also be associated with influenza or may be associated with other viral infections. We are told that colds, flus and intestinal viral infections must run their course and that other than rest and fluids there is not much to be done to speed the healing process. The various symptoms can be treated indiviually with a plethora of prescription and over-the-counter remedies. The cold itself has not yielded to any medication. Additionally, many of the over-the-counter medications given to treat cold and other flu symptoms may cause drowsiness and other side effects which make them undesirable for many potential users.

Vitamin C has been widely used to prevent and treat colds, but recent studies have shown that its effects are questionable at best. The time-worn remedy of chicken soup has been found to actually provide some benefits to cold and flu sufferers.

Other common viral infections include some sore throats and eye inflammations as well as cold sores, canker sores, genital herpes, some lung inflammations and intestinal upsets as noted above. Antibiotics are ineffective against these viral infections and anti-viral medications are often slow acting and may produce unwanted side effects.

Tulin-Silver et al. in U.S. Pat. No. 5,508,282 teaches the application of ascorbic acid in a spray used directly on nasal membranes to shorten the duration of colds. The nasal sprays contain ascorbic acid, caffeine, and other water soluble vitamins and minerals in an aqueous carrier at a pH range of 5.5 to 6.5. These preparations are designed to help repair cell membranes, stimulate the immune system and improve the sense of smell, though the combination taught by Tulin Silver et al. has no effect on the virus itself.

Nasal sprays have also been found effective in delivering large protein molecules such as insulin directly into the body through mucous membranes. The absorption of such polypeptides has been enhanced by the addition of a chelating agent to the nasal spray composition. (U.S. Pat. No. 4,476,116 to Anik) The nasal membrane was chosen as a direct route into the blood stream without resorting to injection and without entering the digestive system where the large protein molecules are broken down by the digestive process. A combination of the nucleoside inosine, lysine ororate and a vitamin, administered orally, has been found to have an anti-inflammatory effect on a variety of mucous membrane diseases such as gastric ulcer, periodontitis, and mouth ulcers. The combination can be administered in aqueous solution or as a gel, capsule or tablet. (U.S. Pat. No. 4,405,610 to Krnjevic') The aqueous solution and gel are examples of the therapeutic agent being delivered to the site of the infection, or close to that site. The particular combinations taught by Krnjevic' do not act on the cause of the inflammation, but on the inflammation itself.

Amino acids such as alanine, glycine, serine, lysine and arginine when added to the gluconate salt solutions of minerals such as zinc resulted in the mineral being absorbed more readily and acting more efficiently on the cellular tissue level in the target organ than when the minerals were administered alone. (U.S. Pat. No. 4,937,234 to Fahim) It appears that these amino acids are being readily absorbed into the cells through interaction with the mineral which assist in its passage through cell membranes.

Lysine has been found very effective in treating and preventing cold sores which are caused by herpes viruses and has also been used to treat genital herpes. The lysine was administered in tablet form. Lysine was also administered intravenously to successfully treat encephalitis. (Saturday Evening Post, November–December 1995 v267 p 54 and p 56) See also "The Metabolic Roles, Pharmacology, and Toxiclolgy of Lysine", N. W. Flodin, J. Am. Coll. of Nutrition, Feb. 1997, pp 7–21. When used in the treatment of cold sores, the tablets were swallowed, not dissolved in the mouth. They had to be taken over long time periods, weeks or months, to be effective. Diets low in arginine and high in lysine also showed promise in treating herpes infections, but again, this regimen was a long term solution.

The administration of a variety of drugs by nasal spray is increasing as a means to introduce such drugs into the bloodstream without having to resort to injection.

Since different viral infections manifest themselves with symptoms in different parts of the body it is believed that there may be a higher concentration of the virus in those specific areas. It makes sense therefore, to concentrate the antiviral therapy in those infected areas. Infections of the mucous membranes caused by non-regenerative viruses may respond readily to such therapies. Combining the nasal spray delivery system with additional applications to the specific areas of infection may provide an even more effective therapy.

The use of lozenges that slowly dissolve in the mouth are well known. Such lozenges when used for a sore throat are usually taken to moisten the throat and to administer a topical anaesthetic to ease the pain. The usual medicaments for a sore throat, antibiotics, are swallowed, not taken in lozenge form. The most common topical administration of a medicament is to treat skin problems such as rashes and allergic reactions, though even these treatments are given more to alleviate the symptoms than to treat the cause. Topical means to treat other types of medical problems are not widespread.

None of the patents or articles described above specifically discuss treatments of viral infections by administration of lysine through nasal sprays, throat sprays, topical drops, lozenges, gums, suppositories, as a microcrystalline powder, or other topical and localized means of application and such applications directly to mucous membranes, nor do they describe combinations of such delivery systems. There is a need for a medicament that can easily be administered directly to the area where the viral infection is concentrated. There is a need for such a medicament that has no inflammatory effect on the body, specifically on mucous membranes, no known toxicity levels and minimal, if any, side effects.

BRIEF SUMMARY OF THE INVENTION

The present invention may provide safe and effective therapies for treating common viral infections such as colds, flu, sore throat, lung congestion, eye inflammations, herpes outbreaks and intestinal disturbances. A solution or suspension of L-lysine monohydrochloride in an aqueous medium or water soluble medium may be administered in a variety of delivery systems such as a spray, inhalant, lozenge, chewing gum, drops, suppository, or enema, or as a topical application such as in a gel or in a combination of two or more of these delivery systems. Lysine in the form of a microcrystalline powder may also be applied to certain target areas. The application of L-lysine monohydrochloride may be made directly to the target areas at regular intervals during the duration of the viral infection.

It is an object of the present invention to provide easily administered preparations that can be used by adults and children to effectively shorten the duration of common viral infections.

It is another object of the present invention to provide preparations with minimal side effects.

It is a further object of the present invention to provide preparations that can prevent or lessen the symptoms of common viral infections if taken at the very onset of such symptoms.

Another object of the present invention is to provide preparations that will shorten the duration of cold sores and other viral lesions.

A further object of the present invention is to provide preparations that can prevent outbreaks of certain viral lesions.

An object of the present invention is to provide the therapeutic agent in combinations of delivery systems resulting in more effective treatment of common viral infections.

Another object of the present invention is to provide a medicament that has a long shelf-life and requires no special storage facilities.

A still further object of the present invention is to provide preparations that are easy to administer and can be carried and used anywhere so the user can continue the therapies throughout the day.

A further object of the present invention is to able to target the therapies to the specific area or areas of high concentration of the virus.

A method for treating viral infections caused by influenza and rhino viruses comprising the step of administering by inhalation to the mucous membranes of the respiratory system of an individual in need of such antiviral therapy an effective dosage of a solution containing from 10 mg to 10,000 mg L-lysine monohydrochloride per 44 ml of an aqueous carrier every one to six hours during the duration of the viral infection whereby the L-lysine monohydrochloride is absorbed directly into the bloodstream through said mucous membranes.

A method for treating viral infections caused by influenza and rhino viruses and causing the symptoms of running nose, cough , sinus inflammation, sore throat and ear fullness comprising the step of administering by inhalation to the mucous membranes of the respiratory system of an individual in needed of such antiviral therapy an effective dosage of a solution containing from 10 mg to 10,000 mg L-lysine monohydrochloride per 44 ml of an aqueous carrier every one to six hours during the duration of the viral infection whereby the L-lysine monohydrochloride is absorbed directly into the bloodstream through said mucous membranes.

A method for treating viral infections caused by influenza and rhino viruses and causing the symptoms of running nose, cough , sore throat and ear fullness comprising the step of administering by inhalation to the mucous membranes of the respiratory system of an individual in need of such antiviral therapy an effective dosage of L-lysine monohydrochloride in the form of a microcrystalline powder every one to six hours during the duration of the viral infection whereby the L-lysine monohydrochloride is absorbed directly in to the bloodstream through said mucous membranes.

A method for treating viral infection caused by influenza and rhino viruses and causing the symptoms of running nose, cough, sore throat, ear fullness and stomach upset comprising the step of administering to the mucous membranes of an individual in need of such antiviral therapy an effective dosage of a solution containing L-lysine monohydrochloride in an aqueous carrier every one to six hours during the duration of the viral infection whereby the L-lysine monohydrochloride is absorbed directly into the bloodstream through said mucous membranes.

A method for treating viral infections caused by influenza and rhino viruses and causing the symptoms of running nose, cough, sore throat, car fullness and stomach upset comprising the step of administering by inhalation to the mucous membranes of the respiratory system of an individual in need of such antiviral therapy an effective dosage of L-lysille monohydrochloride every one to six hours during the duration of the viral infection whereby the L-lysine monohydrochloride is absorbed directly into the bloodstream through said mucous membranes.

A method for treating viral infections caused by influenza and rhino viruses and causing the symptoms of running nose, cough, sore throat, ear fullness and sinus inflamation comprising the step of administering by inhalation to the mucous membranes of an individual in need of such antiviral therapy an effective dosage of L-lysine monohydrochloride every one to six hours during the duration of the viral infection whereby the L-lysine monohydrochloride is absorbed directly into the bloodstream through said mucous membranes.

A method for treating viral infections caused by influenza viruses comprising the step of administering by inhalation to the mucous membranes of the respiratory system of an individual in need of such antiviral therapy an effective dosage of a solution containing from 10 mg to 10,000 mg L-lysine monohydrochloride per 44 ml of an aqueous carrier every one to six hours during the duration of said viral infection whereby the L-lysine monohydrochloride is absorbed directly into the bloodstream through said mucous membranes.

A method for treating viral infections caused by influenza viruses comprising the step of administering by inhalation to the mucous membranes of the respiratory system of an individual in need of such antiviral therapy an effective dosage of L-lysine monohydrochloride every one to six hours during the duration of said viral infection whereby the L-lysine monohydrochloride is absorbed directly into the bloodstream through said mucous membranes.

Other features and advantages of the invention will be seen from the following description and tables.

DETAILED DESCRIPTION OF THE INVENTION

The present invention may be a solution of L-lysine monohydrochloride (hereinafter lysine) in an aqueous medium or water soluble medium or lysine in the form of a microcrystalline powder that may be directed to areas of the body where an infection is concentrated and more specifically to mucous membranes. The lysine may also be taken into the body in the form of a lozenge, gel, gum or suppository. This therapy may be effective when the cause of infection may generally be attributed to non-regenerative viruses.

The crystalline lysine may be ground into a powder and dispersed in the aqueous or water soluble medium. Depending on the concentration used, at least a portion of the lysine may not dissolve but may remain in suspension. The lysine may be ground so finely that even when in suspension the particles may not be readily visible and should not cause any irritation to mucous membranes. When an aqueous medium is used the aqueous solution-suspension will hereinafter be referred to as the "solution", with the understanding that there may be a suspension of the lysine particles present. A water soluble solid or semisolid medium may also be used and finely dispersed particles may also be present along with the dissolved lysine.

The aqueous medium may be distilled water, deionized water, or 0.1% to 0.9% saline solution. A preservative such as phenylcarbinol may be added to the solution. The solution may also be buffered using sodium bicarbonate or other buffering agent to achieve a pH of from 5.0 to 6.0, or such other pH range that may be more indicative of the area of the body being treated. Uses of such preservatives and buffers are well known in the art. The beneficial effects of the solutions were found to be the same for all of the above noted aqueous media.

The solution may be dispensed using an atomizer in the form of a plastic squeeze bottle fitted with an elongated nozzle having a small opening. Such an atomizer may be ideal for administering a nasal or mouth spray. Ideally the solution may be dispersed in a very fine spray or mist that can reach into the upper nasal passages. When sprayed directly into the mouth the spray may make direct contact with the oral mucosa, tongue, throat and tonsils. Drawing the mist down into the lungs may also have a beneficial effect since the increased surface area in the lungs enables additional absorption of the lysine directly into the bloodstream. In all of these uses, the solution may be directed to the infected area, an area which may have a high concentration of the virus.

The atomizer bottles most suitable for nasal and mouth sprays usually contain about 1.5 fluid ounces (oz.) of solution (44 ml). Concentrations of lysine per 1.5 oz. of solution of from 10 mg to 10,000 mg have been used. Good results may be obtained with concentrations of 2000–7000 mg, but the best results may be realized when the lysine is present in the amount of 3000–6000 mg per 1.5 oz. of solution. A typical concentration may be 3500 mg per 1.5 oz. Since there may be undissolved particles present, the solution may be shaken before use for full utilization of the active ingredient.

Containers utilizing pump sprays may also be used to dispense the lysine solutions. Though they may not be as easy to use for nasal administration of lysine they may function well for mouth and throat applications.

The lysine solution may also be dispensed as nasal drops, either using the conventional bulb dropper or by inverting the atomizer bottle and permitting the solution to drip out directly into the nose. The nasal drops may be easier to administer to young children and the dose may be better controlled than by use of the nasal spray.

Though the administration of lysine directly to the infected area by means of the a fine spray may have originally been developed to treat colds and flu, a number of other benefits may be realized. Lysine has been used for several years to treat cold sores. The lysine was administered in tablets which were swallowed, usually several times a day. The dosages were large because most of the lysine entered the digestive tract and never reached the bloodstream. The use of the nasal spray, in addition to oral ingestion of lysine, may increased the efficacy of the oral use in the treatment of cold sores. Spraying the solution directly on cold sores, or applying the solution using a cotton applicator, or by drops, may heal the cold sores much faster than just taking the lysine orally, and without side effects of any kind. This method of application, which may target the area of infection, an area believed to contain high concentrations of the virus, may be much more effective against the virus than oral administration of the same substance. When applied at least every three hours, the topical application may work well without any need to ingest the lysine tablets. Viral sore throats may respond to direct application of lysine by spraying the solution into the mouth and far back into the throat area. Sore throats may also be treated by spraying the solution into both the nose and the mouth with good results.

Administering the lysine directly to the target areas may serve a dual purpose. First, the lysine may be deposited directly on the infected area where it can work on the higher concentration of the virus, and second, the infected areas being all mucous membranes enable the active ingredient to be absorbed directly into the bloodstream. Administering the lysine to nasal membranes and to specific areas of infection may greatly increase the amount of active ingredient entering the bloodstream.

Test subjects with colds or flu used the solutions at varying intervals of from one to four hours. Two sprays in each nostril constituted the usual dose. When the intervals were lengthened to six or more hours the treatment was found to be considerably less effective. All test subjects completed and signed a questionnaire and were advised of the proprietary nature of the test. The identity of the active ingredient was not disclosed.

A group of twenty subjects were each given an atomizer bottle containing 1.5 oz. of 0.65% saline solution containing 3500 mg of lysine prepared according to the above description. They were instructed to use the preparation as soon as possible at the onset of cold or flu symptoms. All agreed to use the spray twice in each nostril every three hours. Their reports are summarized in Tables I, II and III.

TABLE I

| Ten Test Subjects; cold virus; nose inhalation | | | | | |
|---|---|---|---|---|---|
| Relief obtained in: | 1 | 2 | 3 | 4 | (days) |
| Number of subjects reporting: | 5 | 3 | 2 | | |

TABLE II

| Four Test Subjects; cold virus; nose inhalation and mouth inhalation | | | | | |
|---|---|---|---|---|---|
| Relief obtained in: | 1 | 2 | 3 | 4 | (days) |
| Number of subjects reporting: | 3 | 1 | | | |

TABLE III

Six Test Subjects; flu virus; nose inhalation and mouth inhalation

| Relief obtained in: | 1 | 2 | 3 | 4 | (days) |
|---|---|---|---|---|---|
| Number of subjects reporting: | | 2 | 2 | 2 | |

The administration of lysine in the form of a nasal spray was used by other test subjects after being exposed to persons with severe colds, that is persons who were frequently coughing and sneezing. The treatment was continued for at least three days, after which the test subjects reported that they never felt cold symptoms at all.

A test subject used nasal inhalation of lysine every three hours to treat a sore throat and reported relief after one day.

Another test subject who has suffered from throat infections for many years used the lysine spray directly into the throat at the first sign of soreness on at least four occassions. The treatment was repeated every three to four hours for two days. The full sore throat usually experienced after the same soreness never occurred.

Lysine is well known to alleviate or even eliminate outbreaks of cold sores, canker sores, and other herpes infections. However, as previously noted, it was usually administered in the form of tablets which had to be swallowed. Many people have experienced adverse side effects such as gastric distress when high doses of lysine were ingested. This resulted in the treatment being discontinued even when it was initially found to be quite helpful. When lysine is taken orally it passes into the digestive system and is transported by way of the portal circulation to the liver. Only a small percentage of the lysine ingested actually finds its way into the rest of the bloodstream. It is for this reason that oral doses of lysine must be large and the large doses often cause the adverse side effects.

Use of the lysine solution as a nasal spray or mouth spray deposits the lysine on the mucous membranes whereby it may be absorbed directly into the bloodstream. When viral lesions of the oral mucosa are treated by spray, applicator, or dropper directly on the lesion and surrounding tissue, the beneficial result may be attributed to absorption through the mucous membranes with the added effect of targeting the areas of high concentration of the virus. Most of the lysine absorbed may be used by the body, with the initial concentration at the site of the primary infection.

One test subject, with a twenty year history of herpes simplex II outbreaks, reported that use of the nasal spray every three hours for one day stopped the outbreak. Another test subject, with a long history of recurring genital herpes outbreaks, used the nasal spray and the lysine tablets and found that the outbreaks responded much faster than with the tablets alone. This subject also reported that regular use of the nasal spray has prevented herpes outbreaks to the point of almost eliminating them altogether.

Another test subject with a long history of canker sore outbreaks reported that once one canker sore appeared several more usually followed within a day or two. These sores were quite painful and often lasted from five to ten days. The subject was given the lysine solution and told to apply it directly to the lesion. The subject reported that the pain usually associated with the canker sore was alleviated as soon as the solution was applied. The application was repeated every three or four hours until the canker sore was completely healed. The subject reported that this treatment took from three to five days and there was no pain as the lesion healed and no secondary lesions developed. Since this subject has been using the lysine solution the outbreaks of canker sores are infrequent and are healed very quickly.

Certain eye infections have been found to be caused by viruses. These may also be treated with a solution of lysine. The solutions tested contained 100 mg to 4,000 mg in of lysine in 44 ml of solution with the optimum range of 1,000 mg to 3,000 mg in 44ml of solution. A solution prepared specifically for use in the eye may be sterile and may be made in smaller quantities so that it may be discarded after the infection has abated. These solutions should not be reused at a later time.

When lysine is administered by spray solely into the mouth and throat the constant production of saliva may wash the solution into the digestive system too quickly, before it can be fully absorbed into the bloodstream. To increase the time of contact, lysine may be administered in the form of a lozenge that is slowly dissolved directly in the mouth or taken sublingually. In this manner, the lysine may be absorbed through the mucous membranes of the mouth and tongue as well as the throat and tonsils. The lozenge may be made of a water soluble matrix with the finely ground lysine dispersed therein. For some forms of viral infections this slow continuous administration of lysine may provide the best method of treatment. The lysine may be present in a lozenge in concentrations of from 25 mg to 500 mg. An optimum dosage may be 100 mg per lozenge enabling repeated usage during a 24 hour period. The oral and sublingual use of the lozenges may be especially effective in treating oral lesions and may also be beneficial to those people who may find nasal and or mouth sprays distasteful or who may have an acute gagging reflex or other physical disability that would preclude such use.

Lysine may also be administered by means of a chewing gum that releases the lysine slowly into the mouth as it is chewed. When dispensed in a chewing gum the lysine may be released slowly into the saliva which may bathe the oral mucosa, throat and tonsils over a substantial period of time allowing the lysine to be absorbed into the bloodstream before it reaches the digestive tract. Such a chewing gum may contain 25 mg to 500 mg of lysine per portion. Optimum results may be obtained with 100 mg to 200 mg per portion.

The full benefits of lysine treatment for upper respiratory infections may be realized when used in the entire upper respiratory system and nasal passages. Mouth inhalation of the spray may be beneficial, but use of a nebulizer dispensing the same solution may be better for introducing the solution directly into the lungs. The large surface area in the lungs enables greater quantities of lysine to be absorbed directly into the bloodstream in a very short time period.

Often upper respiratory infections settle in the lungs and can cause prolonged discomfort, coughing and heavy chest congestion. When the lysine solution was administered by nebulizer directly into the lungs a test subject found the symptoms to be lessened almost immediately and they cleared up completely within one to three days.

Lysine may also be administered in the form of a microcrystalline powder directly into the lungs by means of a "puffer" or one of the inhalant devices now available. The application of lysine may be from 1 mg to 25 mg per dose, with optimum dosages of 5 mg . A multidose inhalant device may contain from 25 mg to 500 mg as long as each dose delivered is within the given range.

Viral infections effecting the intestinal tract, such as various forms of intestinal flu, may benefit from the direct application of lysine to the infected area. The lysine may be administered rectally using glycerine suppositories containing the finely ground lysine. This may bring the lysine in contact with the mucous membranes lining the large intestine and target the concentration of virus in that area. Such suppositories may contain concentrations of lysine of 10 mg to 500 mg with more effective concentrations of 25 mg to 250 mg in each suppository.

Application of lysine to the large intestine through the use of enemas may also be effective in the treatment of intestinal viruses. As with the suppositories, larger dosages are possible in a single administration. An enema preparation of 500 ml may contain 100 mg to 30,000 mg of lysine.

As previously noted, genital herpes outbreaks have responded to lysine therapy, both by oral ingestion and with the nasal spray. The lysine may also be targeted directly on the areas of infection, the lesions. A gel, of the form used for female personal lubrication may be applied directly to the genital area. Concentrations of from 10 mg to 32,000 mg per ounce of gel, with optimum levels at 12,000 mg per ounce of gel, may be used.

Vaginal suppositories, which may be slow to melt or dissolve, may also provide an effective means of targeting the area of infection. Each suppository may contain 25 mg to 500 mg lysine with optimum dosages at 250 mg to 500 mg.

Any two or more of the above discussed methods of administration of lysine may be combined as needed or as may be comfortable for the user. The large variations or ranges of dosage have been suggested because the preparations may be used for children as well as adults, for persons of different size and weight, and because the dosage may depend on the number of methods of application used together. For example, the nasal spray may be used in conjunction with the lozenges or enema, or any other methods of administration of lysine. The form or forms of use may depend on the personal preference of the user, the particular tolerances of the user, and the nature of the viral infection.

Lysine is a naturally occurring amino acid. It is present in many proteins and released into the body when the proteins are broken down during normal digestion. No toxic levels of lysine have been found. Though the frequency of treatment may be suggested at every three hours, any frequency comfortable to the user may be acceptable.

At times around the clock use of the sprays, drops, inhalers or other means of administration of lysine may not be possible because the subject sleeps through the night. To maintain a therapeutic level of lysine in the bloodstream, a 250 mg to 500 mg dose may be ingested, or taken by other oral administration such as in a lozenge, at bedtime. The specific dose or form of use may depend on whether or not the subject experiences gastric distress from ingestion of lysine.

It is believed that lysine acts by preventing the virus from replicating. Therefore, if the concentration of lysine in the bloodstream can be maintained at high levels, eventually the virus titer may decrease to a level that may be fought by the body's own defenses. The higher the concentration of lysine in the blood, the more effective it may be in preventing the virus from replicating and the faster the body may fight the virus. The application of lysine to the mucous membranes of the nose, mouth, eye, genital area and to the large intestine may permit high concentrations of lysine to be maintained without the side effects realized through ingestion and may target the infected area directly.

As shown above, the use of lysine by targeting the infected areas may shorten the duration of the outbreak and may even prevent illnesses such as colds and sore throats if used directly after contact with an infected person or at the onset of symptoms. Essentially the use of the lysine solution or composition in the nose, mouth and/or lungs, or other specific areas of the body may represent a topical application of lysine to the infected area. Thus, the duration of an infection may be considerably lessened by applying lysine to that infected area. This targeting approach may also be supported by the fast healing response observed when lysine solution was applied directly to cold sores and canker sores in contrast to the time it took to heal the cold sores or canker sores by the ingestion of lysine tablets alone.

While the preferred embodiments of the present invention have been described in detail, it is to be understood that this invention is not limited thereto and may be otherwise practiced within the scope of the following claims.

What is claimed is:

1. A method for treating viral infections caused by influenza and rhino viruses comprising the step of administering by inhalation to the mucous membranes of the respiratory system of an individual in need of such antiviral therapy all effective dosage of a solution containing from 10 mg to 10,000 mg L-lysine monohydrochloride per 44 ml of an aqueous carrier every one to six hours during the duration of the viral infection whereby the L-lysine monohydrochloride is absorbed directly into the bloodstream through said mucous membranes.

2. The method of claim 1 wherein the mucous membranes are the nasal membranes.

3. The method of claim 1 wherein the mucous membranes are the membranes of the mouth and throat.

4. The method of claim 1 wherein the mucous membranes are the membranes of the lungs.

5. The method of claim 1 wherein the solution is administered in the form of a fine mist.

6. A method for treating viral infections caused by influenza and rhino viruses and causing the symptoms of running nose, cough, sinus inflammation, sore throat and ear fullness comprising the step of administering by inhalation to the mucous membranes of the respiratory system of an individual in need of such antiviral therapy an effective dosage of a solution containing from 10 mg to 10,000 mg L-lysine monohydrochloride per 44 ml of an aqueous carrier every one to six hours during the duration of the viral infection whereby the L-lysine monohydrochloride is absorbed directly into the bloodstream through said mucous membranes.

7. The method of claim 6 wherein the mucous membranes are the nasal membranes.

8. The method of claim 6 wherein the mucous membranes are the membranes of the mouth and throat.

9. The method of claim 6 wherein the mucous membranes are the membranes of the lungs.

10. The method of claim 6 wherein the solution is administered in the form of a fine mist.

11. A method for treating viral infections caused by influenza and rhino viruses and causing the symptoms of running nose, cough, sore throat and ear fullness comprising the step of administering by inhalation to the mucous membranes of the respiratory system of an individual in need of such antiviral therapy an effective dosage of L-lysine monohydrochloride in the form of a microcrystalline powder every one to six hours during the duration of the viral infection whereby the L-lysine monohydrochloride is absorbed directly into the bloodstream through said mucous membranes.

12. The method of claim 11 wherein the mucous membranes are the membranes of the lungs.

13. The method claim 12 wherein the microcrystalline powder is administered by means of an inhalant device.

14. The method of claim 13 wherein the inhalant device delivers from 1 mg to 25 mg L-lysine monohydrochloride per dose.

15. A method for treating viral infections caused by influenza and rhino viruses and causing the symptoms of running nose, cough, sore throat, ear fullness and stomach upset comprising the step of administering to the mucous membranes of an individual in need of such antiviral therapy an effective dosage of a solution containing L-lysine monohydrochloride in an aqueous carrier every one to six hours during the duration of the viral infection whereby the L-lysine monohydrochloride is absorbed directly into the bloodstream through said mucous membranes.

16. The method of claim 15 wherein the solution is administered by inhalation to the mucous membranes of the respiratory system.

17. The method of claim 16 wherein the solution contains from 100 mg, to 10,000 mg of L-lysine monohydrochloride per 44 ml of the aqueous carrier.

18. The method of claim 17 wherein the solution is administered in the form of a fine mist.

19. The method of claim 15 comprising the additional step of administering the solution to the mucous membranes of the large intestine.

20. The method of claim 19 wherein the solution contains from 100 mg to 30,000 my of L-lysine monohydrochloride per 500 ml of the aqueous carrier.

21. A method for treating viral infections caused by influenza and rhino viruses and causing the symptoms of running nose, cough, sore throat, ear fullness and stomach upset comprising the step of administering by inhalation to the mucous membranes of the respiratory system of an individual in need of such antiviral therapy an effective dosage of L-lysine monohydrochloride every one to six hours during the duration of the viral infection whereby the L-lysine monohydrochloride is absorbed directly into the bloodstream through said mucous membranes.

22. The method of claim 21 comprising the additional step of administering the L-lysine monohydrochloride to the mucous membranes of the large intestine.

23. The method of claim 22 wherein the L-lysine monohydrochloride is administered by means of a meltable carrier.

24. The method of claim 23 wherein the meltable carrier contains from 10 mg to 500 mg of L-lysine monohydrochloride per dose.

25. A method for treating viral infections caused by influenza and rhino viruses and causing the symptoms of running nose, cough, sore throat, car fullness and sinus inflammation comprising the step of administering by inhalation to the mucous membranes of an individual in need of such antiviral therapy an effective dosage of L-lysine monohydrochloride every one to six hours during the duration of the viral infection whereby the L-lysine monohydrochloride is absorbed directly into the bloodstream through said mucous membranes.

26. The method of claim 25 wherein the L-lysine monohydrochloride is administered to the mucous membranes of the mouth and throat.

27. The method of claim 26 comprising the additional step of administering the L-lysine monohydrochloride by means of a slow dissolving carrier comprising a water soluble matrix containing from 25 mg to 500 mg of L-lysine monohydrochloride whereby the L-lysine monohydrochloride is absorbed slowly, as the carrier dissolves, into an area of high concentration of the virus.

28. The method of claim 26 comprising the additional step of administering the L-lysine monohydrochloride by means of a chewable carrier containing from 25 mg to 500 mg of L-lysine monohydrochloride per portion of said chewable carrier whereby the L-lysine monohydrochloride is absorbed slowly, as it is released from the chewable carrier, into an area of high concentration of the virus.

29. The method of claim 26 wherein L-lysine monohydrochloride is administered in the form of a solution containing from 100 mg to 10,000 mg of L-lysine monohydrochloride per 44 ml of the aqueous carrier.

30. The method of claim 29 wherein the solution is administered in the form of a fine mist whereby the L-lysine monohydrochloride is absorbed into an area of high concentration of the virus.

31. A method for treating viral infections caused by influenza viruses comprising the step of administering by inhalation to the mucous membranes of the respiratory system of all individual in need of such antiviral therapy an effective dosage of a solution containing from 10 mg to 10,000 mg L-lysine monohydrochloride per 44 ml of an aqueous carrier every one to six hours during the duration of said viral infection whereby the L-lysine monohydrochloride is absorbed directly into the bloodstream through said mucous membranes.

32. The method of claim 31 wherein the mucous membranes are the nasal membranes.

33. The method of claim 31 wherein the mucous membranes are the membranes of the mouth and throat.

34. The method of claim 31 wherein the mucous membranes are the membranes of the lungs.

35. The method of claim 31 wherein the solution is administered in the form of a fine mist.

36. A method for treating viral infections caused by influenza viruses comprising the step of administering by inhalation to the mucous membranes of the respiratory system of an individual in need of such antiviral therapy an effective dosage of L-lysine monohydrochloride every one to six hours during the duration of said viral infection whereby the L-lysine monohydrochloride is absorbed directly into the bloodstream through said mucous membranes.

37. The method of claim 36 comprising the additional step of administering the L-lysine monohydrochloride to the mucous membranes of the large intestine.

38. The method of claim 37 wherein the L-lysine monohydrochloride is administered in the form of an aqueous solution.

39. The method of claim 38 wherein the solution contains from 100 mg to 30,000 mg of L-lysine monohydrochloride per 500 ml of an aqueous carrier.

40. The method of claim 36 wherein the mucous membranes are the membrane of the lungs.

41. The method of claim 40 wherein the L-lysine monohydrochloride is administered in the form of a microcrystalline powder.

42. The method of claim 41 wherein the microcrystalline powder is administered by means of an inhalant device.

43. The method of claim 42 wherein the inhalant device delivers from 1 mg to 25 mg of L-lysine monohydrochloride per dose.

* * * * *